United States Patent [19]

Ziegler

[11] Patent Number: 4,704,363
[45] Date of Patent: Nov. 3, 1987

[54] FERMENTATION SYSTEM

[75] Inventor: Heinrich Ziegler, Rutschwil, Switzerland

[73] Assignee: Sulzer Brothers Limited, Winterthur, Switzerland

[21] Appl. No.: 917,016

[22] Filed: Oct. 9, 1986

[30] Foreign Application Priority Data

Oct. 28, 1985 [CH] Switzerland ............... 4632/85

[51] Int. Cl.⁴ ............................................. C12M 1/04
[52] U.S. Cl. ..................................... 435/313; 55/199; 55/206; 55/463
[58] Field of Search ............... 435/313; 55/199, 201, 55/206, 463

[56] References Cited

U.S. PATENT DOCUMENTS 4,181,576  1/1980  Malick ........................... 435/313

Primary Examiner—Carroll B. Dority, Jr.
Attorney, Agent, or Firm—Kenyon & Kenyon

[57] ABSTRACT

The fermentation system is provided with a separating section in which a plurality of vertically disposed inserts are positioned to form narrow upwardly directed passages for the flow of the fermentation mixture. The inserts serve to impart high shear forces on the mixture so as to reduce the viscosity of the mixture and thus release the gas in the form of bubbles. A collecting chamber is provided to collect the gas and the chamber is vented for the removal of the gas from the fermentation circuit.

13 Claims, 4 Drawing Figures

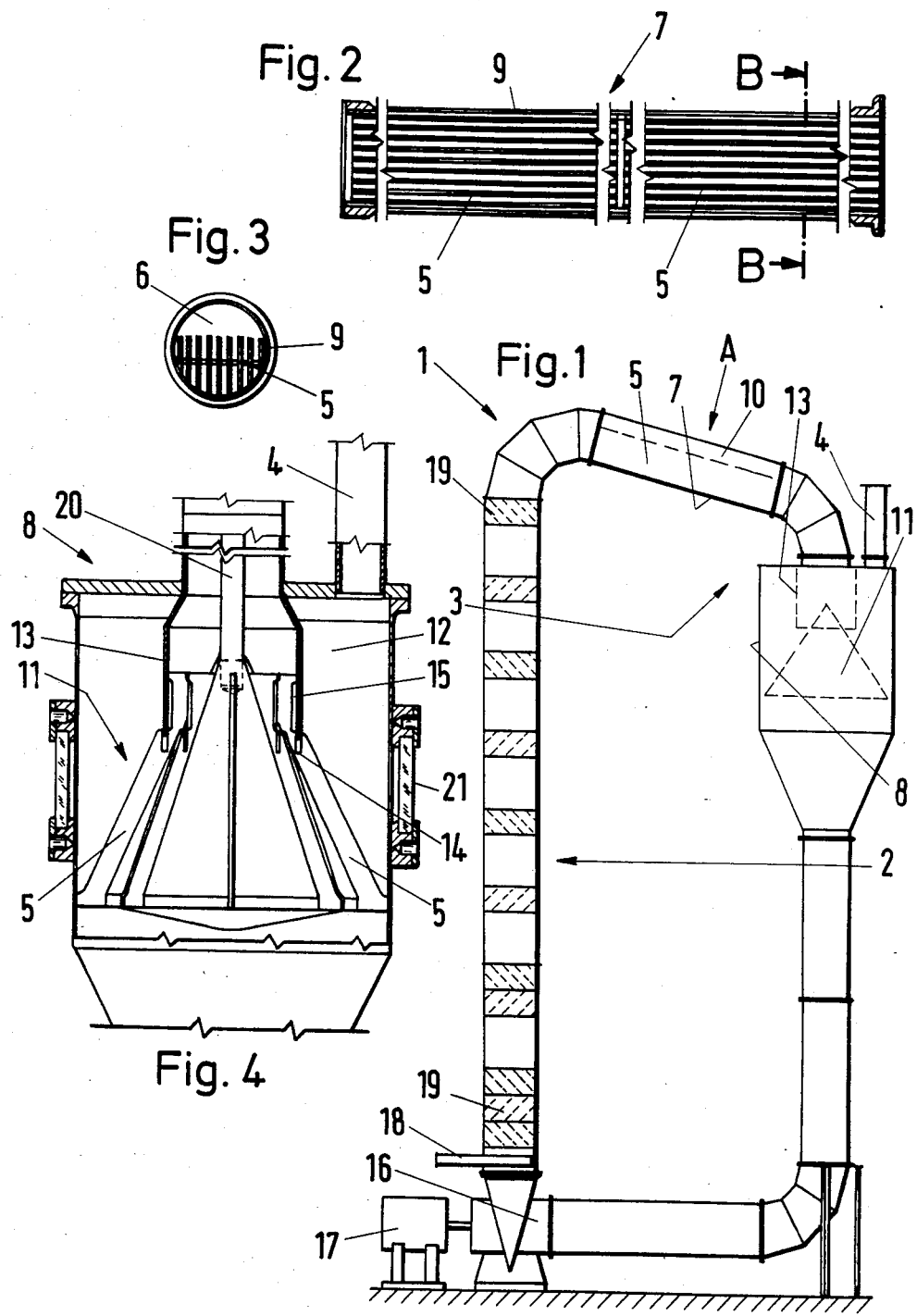

FERMENTATION SYSTEM

This invention relates to a fermentation system. More particularly, this invention is directed to a fermentation system for an aerobic fermentation process.

Heretofore, various types of fermentation system have been known for conducting various processes, for example for performing aerobic fermentation processes. One known system includes a pipe circuit through which a high-viscosity, non-newtonian (pseudoplastic) liquid fermentation mixture is forced by a circulating pump. In addition, the circuit has been provided with one section for gasifying and mixing the fermentation mixture, a second section for separating the gas which has formed during the gasifying and mixing of the mixture and a means for removing the gas from the fermentation system. The term "pseudoplastic liquid or mixtures" is intended to include all liquids in which shearing forces bring about a "liquefaction", that is, a reduction of viscosity, regardless of whether this effect occurs immediately or only after a threshold for the shearing forces is exeeded and regardless of whether or not a hysteresis occurs when the shearing force abates.

Where the systems are used for aerobic fermentation, the necessary gas/liquid oxygen transfer and the respective carbon dioxide desorption is carried out during gasifying and mixing in the first section of the system. Thereafter, the gas phase which is depleted in oxygen and enriched with carbon dioxide is separated in a gas/liquid separating unit in the second section to a large extent. In addition, for high-viscosity, non-newtonian fermentation mixtures as frequently occur, for example, in the preparation of antibotics and enzymes as well as in the production of biologic polymers such as xanthane, use has also been made of inserts such as static mixing elements, in the gasified first section in order to dissipate the introduced energy homogeneously over the entire cross section and thus achieve a homogeneous dispersion of the gas phase and an intensive substance exchange in the fermentation mixture.

However, in the case of the high viscosity, non-newtonian fermentation mixtures, a problem resides in separation of the gas phase from the fermentation mixture. Specifically, this must take place under sterile conditions and with a short stay in the separating unit. The previously known gas/liquid separating units which are described and recommended in the trade literature have been unable to solve this problem.

In some cases, the separating units have been provided with arrangements which rely upon a separating action due to deceleration of the fluid viscosity. However, these arrangements are not suitable since the buovancy of the gas bubbles is too low to rise through a layer (bed) of the high- viscosity liquid or suspension. Moreover, the decleration in such arrangements causes an increase of the apparent viscosity of the liquid phase in the pseudoplastic liquids, thus, making degasification rather more difficult.

On the other hand, separating units which rely upon the effect of centrifugal force such as cyclones and the like, are not able to solve the problem of separation. This is because the velocity of the liquid decreases rapidly after entrance into the separating unit due to the increased viscosity. Thus, the expected operation of such a separating unit never comes into play.

Accordingly, it is an object of the invention to provide a system for reliably removing gas from a high viscosity non-newtonian liquid fermentation mixture.

It is another object of the invention to provide a relatively simple separating unit for separating gas from a gasified fermentation mixture.

It is another object of the invention to provide a simple structure for removing gas from a gasified fermentation mixture without the need for a great degree of supervision.

Briefly, the invention provides a fermentation system wherein a high viscosity non-newtonian liquid fermentation mixture is pumped by a circulation pump through a pipe circuit. In addition, the pipe circuit has a first section for gasifying and mixing the fermentation mixture and a second section communicating with the first section in order to receive the fermentation mixture.

In accordance with the invention, a plurality of inserts are provided in the second section to define a plurality of narrow vertical passages for shearing the fermentation mixture in order to reduce the viscosity of the fermentation mixture and to release a gas therefrom. In addition, a collecting chamber is provided in the pipe circuit for collecting the gas and means communicate with this chamber for removing the gas from the circuit.

The separation of the gas phase from the gasified fermentation mixture is caused by the reduction in the viscosity of the mixture due to the intensive action of the shearing forces as the mixture flows through the narrow upwardly opened passages defined by the inserts. During this time, the gases which are dispersed in the mixture rise through the mixture bed under their own buoyancy upwardly into the collecting chamber. In this respect, the natural buoyancy of the gas bubbles, despite the high viscosity fermentation mixture, is sufficient to make the bubbles rise and to permit relatively large gas agglomerations to form.

The section in which the gas is separated may include a pair of sequentially disposed assemblies for separating the gas in two stages. For example, one assembly includes a pipe section for conducting a flow of the fermentation mixture and the inserts are disposed in this pipe section with vertical parallel walls and with a collecting chamber arranged above the walls. The second assembly may include a vertically disposed pipe section for receiving a flow of the fermentation mixture as well as a bell-like conical part vertically disposed in the vertical pipe section for conducting the fermentation mixture thereover. In this assembly, inserts are also mounted circumferentially on the conical part in order to define the narrow passages for the shearing of the fermentation mixture. In addition, a collecting chamber is disposed annularly above the inserts within the pipe section to collect the separated gas.

These and other objects and advantages of the invention will become more apparent from the following detailed description taken in conjunction with the accompanying drawings wherein:

FIG. 1 schematically illustrates a fermentation system constructed in accordance with the invention;

FIG. 2 illustrates a first assembly in axial section from the perspective of arrow A in FIG. 1;

FIG. 3 illustrates a view taken on line B—B of FIG. 2; and

FIG. 4 illustrates a cross sectional of a second assembly for separating out gas in accordance with the invention.

Referring to FIG. 1, the fermentation system is constructed, for example for the fermentation of high-viscosity, non-newtonian (pseudoplastic) fermentation mixtures. As indicated, the system employs a pipe circuit 1 in which the fermentation takes place as the mixture is circulated in the circuit by means of a circulation pump 16. As indicated, the pump 16 is driven by a motor 17 so as to pump the liquid fermentation mixture through the circuit 1.

The pipe circuit 1 has a vertical section 2, as viewed, for gasifying and mixing the fermentation mixture. To this end, a pipe 18 is connected to the lower end of the section 2 so that air can be blown into the section 2 in order to supply the oxygen needed for fermentation. This air is usually a sterile filtered air which is injected in amounts sufficient to be mixed with the fermentation mixture to cause the desired reaction. In addition, a series of static mixing elements 19 are disposed within the mixing section 2 so that the introduced energy is dissipated over the entire pipe cross section. Thus, a homogeneous dispersion of the gaseous phase and an intensive substance exchange in the fermenting mixture to be treated is achieved.

During the reaction which occurs in the gasifying and mixing section 2, gases are formed which must be removed from the fermentation mixture continuously, that is, with every cycle through the circuit 1. This occurs in a subsequent separating section 3 which is constructed to separate the gas mixture formed during gasifying and fermenting from the fermentation mixture. The separating section 3 also communicates with a means such as a vent pipe 4 for the removal of the gas mixture from the fermentation system.

The fermentation mixture which is degased in the separating section 3 is delivered to the pump 16 for recycling into the mixting section 2 for gasifying and mixing again.

The various pieces of equipment which are customary in a fermentation system of the above type have been omitted in the drawings for purposes of simplification. Such equipment includes mainly waste gas coolers, sterile filters for air, various heat exchangers for heating or cooling or temperature maintenance of a fermentation mixture, various proportioning devices for feeding additives such as acid, base or anti-foamants to the fermentation mixture as well as various measuring and regulating devices. Also not shown is any sterile filter in the vent pipe 4 which may optionally lead to a waste gas anaylizer.

As indicated in FIG. 1, the separating section 3 includes a pair of sequentially disposed assemblies 7, 8 for separating the gas in two stages.

Referring to FIGS. 1, 2 and 3, the first assembly 7 includes a pipe section 9 for conducting a flow of the fermentation mixture from the gasifying and mixing section 2 to the second assembly 8. As indicated, the pipe section 9 is downwardly inclined so as to receive the fermentation mixture at the upper end and to discharge the mixture from the lower end. In addition, a plurality of inserts 5 are disposed within the pipe section in order to define a plurality of narrow vertical passages for shearing the fermentation mixture in order to reduce the viscosity of the mixture and to release the gas therefrom. As indicated in FIG. 3, each insert 5 has vertical walls and the inserts are disposed in parallel to each other in vertical planes. Further, the inserts do not extend to the upper limit of the pipe section 9 but rather terminate within the pipe section 9 so that a collecting chamber 6 is formed.

During operation, the viscosity of the mixture is reduced by the shearing section of the walls of the inserts 5 between which the mixture must necessarily pass driven by the action of the circulating pump 16. The shearing forces reduce the viscosity of the mixture to such a degree that the gases dispersed in the mixture are able to rise through the mixture bed by their own buoyance into the collecting chamber 6. Since the mixture within the collecting chamber is practically no longer exposed to any shearing forces, the bubbles of gas which rise into the collecting chamber 6 grow to form larger gas agglomerations and finally detach firmly from the liquid fermentation mixture. During this time, the fermentation mixture within the collecting chamber is also enriched with the gas bubbles.

By way of example, an existing experimental plant was arranged with the inserts arranged at a mutual distance of 10 millimeters. Generally speaking, the distance between the individual inserts is chosen advantageously in a process-specific manner, i.e. chiefly depending on the viscosity properties of the mixture to be degased and on the desired degree of degasing. According to the physics of pseudoplastic mixtures, a major reduction of the apparent viscosity is obtained only in the boundary layer near the insert wall, so that effective degasing is possible only in this region. The boundary layer thickness depends on the rheological (flow) behavior of the respective liquid or mixture. Optimum degasing is achieved if the channel width approximately corresponds to double the boundary layer thickness. In the practice, however, this may be difficult to realize, uneconomical or unnecessary, depending on the rheological behavior of the fermentation mixture. In the plant referred to, which was used for the production of a biopolymer, it was possible at the mentioned spacing of the inserts 5 to lower the gas volume proportion in the mixture consistently to less than 2%. The liquid phase contained a concentration of 40 g/lt of biopolymer, which led to typically pseudoplastic flow behavior. The apparent viscosities, measured in a cylinder viscosimeter (Contraves Rheomat 15) were at $_s{-1}$ a shearing gradient D of 700 $s^{-1}$ 0.12 Pa s, at a D of 200 $S^{-1}$ 0.55 Pa s and at a D of 27 $s^{-1}$ 8.25 Pa s.

Referring to FIGS. 1 and 4, the second assembly 8 is vertically disposed so as to receive the mixture from the inclined pipe section 9 (FIG. 2). To this end, care is taken not to have a large bend of the connecting piece between the two assemblies 7, 8 so as to avoid remixing of the liquid with the gas under the action of centrifugal force. Thus, the bend should be as small as possible and, thus, the pipe section 9 is inclined in order to keep the bend of the connecting piece small.

Referring to FIG. 4, the second assembly 8 includes a vertically disposed pipe section having a cover at the top to define a closed collecting chamber 12, a vertically disposed bell-like conical part 11 and a second pipe section 13 of smaller diameter through which the fermentation mixture is delivered from the connecting piece. As indicated, the conical part 11 is disposed coaxially with the inner pipe section 13 so that the fermentation mixture flows over the conical part 11. In addition, a plurality of inserts 5 are disposed circumferentially about the conical part 11. These inserts 5 are oriented along the generating lines of fall of the conical part 11 to form narrow passages which are open upwardly into the empty collecting chamber 12. Since the inserts 5 are not parallel to each other, it is possible, and in some cases necessary, to provide additional vertical partitions at the lower ends of the passages in order to narrow the passages and thus maintain the respective intensive shear between the inserts 5. In the previously mentioned experimental plant, a mean distance of about 10 millimeters was maintained between the inserts 5 in the second assembly 8.

As indicated in FIG. 4, the vent pipe 4 communicates with the collection chamber 12.

Further, as indicated in FIG. 4, the conical part 11 has an apex coaxially within the inner pipe section 13 in order to define an annular gap therebetween. In addition, the conical part 11 is connected to a rod 20 which is vertically adjustable so that the conical part 11 can be displaced vertically relative to the pipe section 13 in order to adjust the size of the gap formed between the lower edge 14 of the pipe section 13 and the surface of the conical part 11. The significance of this adjustment of the gap between the pipe section 13 and the conical part 11 is that a pressure gradient as well as a velocity gradient of the flowing fermentation mixture can be adjusted. In order to permit this vertical displacement of the conical part 11 with the inserts 5, the lower edge 14 of the pipe section 13 is formed with a plurality of circumferentially disposed slits 15 aligned with and receiving the inserts 5.

It is conceivable that the separation of the gaseous phase from the fermentation mixture could, in some cases, be achieved by the action of the shearing forces on the conical part 11. However, particularly with high viscosity, non-newtonian mixtures, the flow along the narrow passages would either take too long since a short stay is desirable or drainage problems might arise in the narrow passages. Thus, the assembly 7 precedes the assembly 8 so that the fermentation mixture can be subjected to a forced flow within the first assembly 7 wherein a very intensive shear and a first phase of the separation of the gaseous phase takes place before the mixture arrives on the conical part 11 to complete the separation.

As indicated in FIG. 4, inspection ports 21 may be provided in the outer pipe section 13 in order to check the progress of the process in the second assembly 8.

Of note, a number of constructions based upon the above described principle are conceivable. For example, it is conceivable to provide arrangements which are based upon the use of centrifugal forces. Further, it is possible to modify the first assembly 7 with vertical walls as shown in FIG. 3 which form zig-zag passages so that a more intensive shearing of the fermentation material would result due to the turns in the zig-zag path by the action of centrifugal forces at a considerable flow velocity of the fermentation material.

During operation, the pump 16 serves to pump the fermentation mixture through the gasifying and mixing section 2 where the mixture and the air delivered through the pipe 18 are mixed together in a homogeneous fashion. Thereafter, the gasified mixture flows into the pipe section 9 of the first assembly 7. A mixture is then subjected to shearing within the narrow passages formed by the vertical inserts 5 so that gas bubbles form and begin to rise. By the time the mixture arrives at the lower end of the assembly 7, a significant quantity of gas bubbles should have risen into the collecting chamber 6 to enrich the fermentation mixture chamber therein.

Thereafter, the fermenatation mixture is deliverd into the vertical assembly 8 by flowing through the pipe section 13 directly onto the conical part 11. The gas in the enriched portion of the mixture is then caused to separate due to the shaping of the conical part 11 as well as the inserts 5 thereon. The separated gas then passes upwardly into the collecting chamber 12 and is vented through the vent pipe 4. The gas depleted mixture then falls from the conical part 11 into the remainder of the assembly 8 and is delivered to the pump 18 from which the mixture is recycled.

The invention thus provides a relatively simple structure for separating gas from a gasified fermentation mixture.

Further, the invention provides for the reliable separation of a gas from the high viscosity non-newtonian fermentation mixture which does not require a large amount of supervision.

In the preceding specification the term "a short stay in the separating unit" is intended for retention times up to few minutes, especially up to one minute, in the unit.

What is claimed is:

1. A fermentation system comprising
a pipe circuit having a first section for gasifying and mixing a fermentation mixture, a second section communicating with said first section to receive the fermentation mixture, a plurality of inserts in said second section defining a plurality of narrow vertical upwardly opened passages for shearing the fermentation mixture to reduce the viscosity of the fermentation mixture and to release a gas therefrom, a collecting chamber for collecting the gas, and means communicating with said chamber for removing the gas from said circuit; and
a circulation pump for pumping a high viscosity non-newtonian liquid fermentation mixture through said circuit.

2. A fermentation system as set forth in claim 1 wherein said inserts have vertical walls defining said passages therebetween.

3. A fermentation system as set forth in claim 1 wherein said second section includes a pair of sequentially disposed assemblies for separating the gas in two stages.

4. A fermentation system as set forth in claim 3 wherein one of said assemblies includes a pipe section for conducting a flow of the fermentation mixture and said inserts have vertical parallel walls within said pipe section defining said passages therebetween.

5. A fermentation system as set forth in claim 3 wherein one of said assemblies includes a vertically disposed pipe section for receiving a flow of the fermentation mixture and a bell like conical part vertically disposed in said pipe section for conducting the fermentation mixture thereover, said inserts being mounted circumferentially on said conical part to define said passages therebetween and said collecting chamber is disposed annularly above said inserts within said pipe section.

6. A fermentation system as set forth in claim 5 which further comprises a second pipe section within said vertically disposed pipe section to conduct the fermentation therethrough and wherein said conical part has an apex coaxially within said second pipe section to define an annular gap therebetween and is vertically displaceable relative to said second pipe section to adjust said gap.

7. A fermentation system as set forth in claim 6 wherein said second pipe section has a plurality of circumferentially disposed slots aligned with and receiving said inserts.

8. A fermentation system as set forth in claim 3 wherein one assembly includes a first pipe section for conducting a flow of the fermentation mixture and said inserts having vertical parallel walls within said pipe section defining said passages therebetween and a second assembly includes a second vertically disposed pipe section for receiving the fermentation mixture from said first pipe section, a conical part vertically disposed in said second pipe section for conducting the fermentation mixture thereover, a plurality of inserts mounted circumferentially on said conical part to define said passages therebetween and a collecting chamber disposed above said inserts within said second pipe section for collecting gas from the mixture.

9. In a fermentation system, the combination comprising
 a first section for gasifying and mixing a high viscosity non-newtonian liquid fermentation mixture therein;
 a second section communicating with said first section to receive the fermentation mixture;
 a plurality of inserts in said second section defining a plurality of narrow vertical passages for shearing the fermentation mixture to reduce the viscosity of the fermentation mixture and to release a gas therefrom; and
 means for removing the gas from said second section.

10. The combination as set forth in claim 9 wherein said inserts have vertical walls defining said passages therebetween.

11. The combination as set forth in claim 9 wherein said second section includes a pair of sequentially disposed assemblies for separating the gas in two stages.

12. The combination as set forth in claim 11 wherein one of said assemblies includes a pipe section for conducting a flow of the fermentation mixture and said inserts have vertical parallel walls within said pipe section defining said passages therebetween.

13. The combination as set forth in claim 11 wherein one of said assemblies includes a vertically disposed pipe section for receiving a flow of the fermentation mixture and a bell-like conical part vertically disposed in said pipe section for conducting the fermentation mixture thereover, said inserts being mounted circumferentially on said conical part to define said passages therebetween and said collecting chamber is disposed annularly above said inserts within said pipe section.

* * * * *

UNITED STATES PATENT AND TRADEMARK OFFICE
CERTIFICATE OF CORRECTION

PATENT NO. : 4,704,363
DATED : November 3, 1987
INVENTOR(S) : HEINRICH ZIEGLER

It is certified that error appears in the above-identified patent and that said Letters Patent is hereby corrected as shown below:

```
Column 1, line 24 "forces" should be  -force-
Column 1, line 24 "exeeded" should be -exceeded-
Column 1, line 35 "antibotics" should be -antibiotics-
Column 1, line 56 "buovancy" should be -buoyancy-
Column 1, line 58 "decleration" should be -deceleration-
Column 2, line 66 "cross sectional" should be -cross sectional
     view-
Column 3, line 37 "mixting" should be -mixing-
Column 3, line 50 "anaylizer" should be -analyzer-
Column 4, line 10 "buoyance" should be -buoyancy-
Column 4, line 43 delete "s$^{-1}$"
Column 4, line 45 "S" should be -s-
Column 5, line 67 "fermenatation" should be -fermentation-
```

Signed and Sealed this

Seventeenth Day of May, 1988

*Attest:*

DONALD J. QUIGG

*Attesting Officer*     *Commissioner of Patents and Trademarks*